US008180445B1

(12) United States Patent
Moffitt

(10) Patent No.: US 8,180,445 B1
(45) Date of Patent: May 15, 2012

(54) USE OF INTERPHASE TO INCREMENTALLY ADJUST THE VOLUME OF ACTIVATED TISSUE

(75) Inventor: Michael A. Moffitt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1214 days.

(21) Appl. No.: 11/694,892

(22) Filed: Mar. 30, 2007

(51) Int. Cl.
*A61N 1/36* (2006.01)

(52) U.S. Cl. ............... 607/2; 607/1; 607/59; 607/72; 607/74; 607/115; 607/116; 607/117; 607/118

(58) Field of Classification Search .......... 607/1–2, 607/59, 72, 74, 115–118
See application file for complete search history.

(56) References Cited

U.S. PATENT DOCUMENTS

| | | | |
|---|---|---|---|
| 3,727,616 A * | 4/1973 | Lenzkes | 607/59 |
| 6,516,227 B1 | 2/2003 | Meadows et al. | |
| 6,895,280 B2 | 5/2005 | Meadows et al. | |
| 6,909,917 B2 | 6/2005 | Woods et al. | |
| 6,920,359 B2 | 7/2005 | Meadows et al. | |
| 6,993,384 B2 | 1/2006 | Bradley et al. | |
| 7,539,538 B2 | 5/2009 | Parramon et al. | |
| 2003/0139781 A1 | 7/2003 | Bradley et al. | |
| 2003/0204221 A1 | 10/2003 | Rodriguez et al. | |
| 2005/0267546 A1 | 12/2005 | Parramon et al. | |
| 2006/0190053 A1 | 8/2006 | Dobak | |
| 2006/0241721 A1 | 10/2006 | Kothandaraman et al. | |
| 2007/0038250 A1 | 2/2007 | He et al. | |
| 2007/0066995 A1 * | 3/2007 | Strother et al. | 607/2 |

OTHER PUBLICATIONS

Gorman, P.H., et al., "The Effect of Stimulus Parameters on the Recruitment Characteristics of Direct Nerve Stimulation", IEEE Transactions on Biomedical Engineering, vol. BME-30, No. 7, Jul. 1983, pp. 407-414.
Kuncel, A.M., et al., "Selection of Stimulus Parameters for Deep Brain Stimulation", Clinical Neurophysiology 115 (2004) 2431-2441.
PCT International Search Report for PCT/US2008/058774, Applicant: Boston Scientific Neuromodulation Corporation, Form PCT/ISA/210 and 220, dated Jul. 17, 2008 (6 pages).
PCT Written Opinion of the International Search Authority for PCT/US2008/058774, Applicant: Boston Scientific Neuromodulation Corporation, Form PCT/ISA1237, dated Jul. 17, 2008 (8pages).

(Continued)

*Primary Examiner* — Carl H Layno
*Assistant Examiner* — Deborah Malamud
(74) *Attorney, Agent, or Firm* — Vista IP Law Group LLP

(57) ABSTRACT

A neurostimulation system comprises one or more electrical contacts, output stimulation circuitry capable of outputting a multiphasic waveform (e.g., a biphasic waveform) to the electrical contact(s), and control circuitry capable of varying an interphase of the multiphasic stimulation waveform. The control circuitry may also be capable of varying an amplitude of the multiphasic waveform. In this case, the control circuitry may be capable of discretely varying the amplitude of the multiphasic stimulation energy in a plurality of low-resolution steps, and may further be capable of varying the interphase of the multiphasic stimulation energy between the low-resolution steps; for example, by discretely varying the interphase in a plurality of high-resolution steps between each adjacent pair of low-resolution steps.

25 Claims, 10 Drawing Sheets

OTHER PUBLICATIONS

The Deep-Brain Stimulation for Parkinson's Disease Study Group, "Deep-Brain Stimulation of the Subthalamic Nucleus or the Pars Interna of the Globus Pallidus in Parkinson's Disease", N Engl J Med, vol. 345, No. 13, Sep. 27, 2001, pp. 956-963.

PCT International Preliminary Report on Patentability (Chapter I of the Patent Cooperation Treaty) for PCT/US2008/058774, Applicant: Boston Scientific Neuromodulation Corporation, Form PCT/IB/326 and 373, dated Oct. 6, 2009 (10 pages).

EPO Communication dated Nov. 7, 2011, in European Patent Application No. 08744686.0-2305, Applicant: Boston Scientific Neuromodulation Corporation, (4pages).

* cited by examiner

*152*

| State (#) | A(μa) | t(μa) |
|---|---|---|
| 1 | 100 | 0 |
| 2 | 100 | 10 |
| 3 | 100 | 20 |
| 4 | 100 | 30 |
| 5 | 100 | 40 |
| 6 | 200 | 0 |
| 7 | 200 | 10 |
| 8 | 200 | 20 |
| 9 | 200 | 30 |
| 10 | 200 | 40 |
| 11 | 200 | 50 |
| 12 | 200 | 60 |
| 13 | 300 | 0 |
| 14 | 300 | 10 |
| 15 | 300 | 20 |
| 16 | 300 | 30 |

1 { rows 1-5, 2 { rows 6-12, 3 { rows 13-16

| State (#) | A(μa) | t(μa) |
|---|---|---|
| 1 | 100 | 0 |
| 2 | 100 | 10 |
| 3 | 100 | 20 |
| 4 | 100 | 30 |
| 5 | 100 | 40 |
| 6 | 100 | 50 |
| 7 | 200 | 30 |
| 8 | 200 | 40 |
| 9 | 200 | 50 |
| 10 | 200 | 60 |
| 11 | 300 | 10 |
| 12 | 300 | 20 |
| 13 | 300 | 30 |
| 14 | 300 | 40 |
| 15 | 300 | 50 |
| 16 | 300 | 60 |

1 { rows 1-6, 2 { rows 7-10, 3 { rows 11-16

FIG. 17

USE OF INTERPHASE TO INCREMENTALLY ADJUST THE VOLUME OF ACTIVATED TISSUE

FIELD OF THE INVENTION

The present invention relates to tissue stimulation systems, and more particularly, to a system and method for adjusting the volume of activated tissue.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications, such as angina pectoris and incontinence. Deep Brain Stimulation (DBS) has also been applied therapeutically for well over a decade for the treatment of refractory Parkinson's Disease, and DBS has also recently been applied in additional areas, such as essential tremor and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more electrode carrying stimulation leads, which are implanted at the desired stimulation site, and a neurostimulator implanted remotely from the stimulation site, but coupled either directly to the stimulation lead(s) or indirectly to the stimulation lead(s) via a lead extension. Thus, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., pain relief), while minimizing the volume of non-target tissue that is stimulated. A typical stimulation parameter set may include the electrodes that are sourcing (anodes) or returning (cathodes) the stimulation pulses at any given time, as well as the magnitude, duration, and rate of the stimulation pulses. The neurostimulation system may further comprise a handheld patient programmer to remotely instruct the neurostimulator to generate electrical stimulation pulses in accordance with selected stimulation parameters. The handheld programmer may, itself, be programmed by a technician attending the patient, for example, by using a Clinician's Programmer Station (CPS), which typically includes a general purpose computer, such as a laptop, with a programming software package installed thereon.

Typically, the volume of activated tissue in any given neurostimulation application may be increased or decreased by adjusting certain stimulation parameters, such as amplitude and pulse width. However, the size of the volume of activated tissue is not modified in a continuous fashion, but rather in a discrete fashion, where the step sizes of the increasing or decreasing stimulation energy are constrained by the amplitude and pulse width resolutions permitted by the hardware used to generate the stimulation energy. Insufficient resolution is a problem in applications where tissue associated with the therapy and the tissue associated with undesirable side effects are juxtaposed, such as in DBS or SCS. That is, given the current resolution of the stimulation hardware, it may be difficult to stimulate the target tissue that provides the therapeutic relief without also stimulating the tissue that causes the side effects.

Evidence exists that the current hardware resolution used to increase or decrease the volume of activation in DBS with existing Food and Drug Administration (FDA) approved devices is too large. For example, in subthalamic nucleus (STN) stimulation, clinicians typically use pulse widths close to the short end of the available range (60 μs minimum)(See The Deep-Brain Stimulation for Parkinson's Disease Study Group, *Deep-Brain Stimulation of the Subthalamic Nucleus or the Pars Interna of the Globus Pallidus in Parkinson's Disease*, N Engl J Med, Vol. 345, No. 13, Sep. 27, 2001), and one candidate possibility for the use of short pulse widths is that they allow smaller changes in the volume of activation for a given amplitude step size (e.g., the Kinetra® IPG allows 0.05V steps, and the Precision® IPG allows 100 μA steps) than do large pulse widths. See Gorman and Mortimer, *The Effect of Stimulus Parameters on the Recruitment Characteristics of Direct Nerve Stimulation*, IEEE Transactions on Biomedical Engineering, Vol. BME-30, No. 7, July 1983.

FIG. 1 simplistically illustrates a problem that may result from having a stimulation resolution that is too low to adequately stimulate target tissue T without stimulating non-target tissue NT. As there shown, stimulation energy is applied to an electrode E at two increasing amplitudes (A1, A2, and A3) to create three increasing volumes of activated tissue (V1, V2, and V3). The stimulation energy applied to the electrode E at amplitude A2, although not stimulating the non-target tissue, is inadequate to include the entire target tissue within the volume of activated tissue V2, thereby failing to optimize the therapy provided to the patient. The stimulation applied to the electrode E at amplitude A3, while sufficient to include the entire target tissue T within the volume of activated tissue V3, also includes the non-target tissue NT, thereby potentially creating undesirable side effects.

There, thus, remains a need for a neurostimulation method and system modifying a volume of activation with an increased resolution.

SUMMARY OF THE INVENTION

In accordance with a first aspect of the present inventions, a method of providing therapy to a patient is provided. The method comprises placing one or more electrodes in contact with tissue of a patient, delivering multiphasic (e.g., biphasic) stimulation energy to the electrode(s), thereby activating a volume of the tissue, and modifying the volume of activated tissue by varying an interphase of the multiphasic stimulation energy being delivered to the electrode(s).

In one method, the multiphasic stimulation energy comprises a cathodic pulse and an anodic pulse, with the interphase being between the cathodic pulse and the anodic pulse. The cathodic pulse may precede the anodic pulse. In another method, the multiphasic stimulation energy comprises a stimulation pulse and a recharge pulse, with the interphase being between the stimulation pulse and the recharge pulse. In still another method, the multiphasic stimulation energy comprises a stimulation pulse having a pulse width less than 100 μs, and the interphase of the multiphasic energy is varied in the range of 0 μs-100 μs.

An optional method further comprises varying an amplitude of the multiphasic stimulation energy being delivered to the electrode(s) to modify the volume of activated tissue. In this case, the amplitude of the multiphasic stimulation energy may be discretely varied in a plurality of steps, and the interphase of the multiphasic stimulation energy may be varied between the plurality of steps. For example, the amplitude variation may modify the volume of activated tissue in low resolution steps, and the interphase variation may modify the volume of activated tissue in high resolution steps between the low resolution steps.

In accordance with a second aspect of present inventions, a neurostimulation system is provided. The neurostimulation system comprises one or more electrical contacts. In one embodiment, the neurostimulation system may comprise a stimulation lead carrying one or more electrodes electrically coupled to the electrical contact(s). The neurostimulation system further comprises output stimulation circuitry capable of outputting a multiphasic waveform (e.g., a biphasic waveform) to the electrical contact(s), and control circuitry capable of varying an interphase of the multiphasic stimulation waveform.

In one embodiment, the multiphasic waveform comprises a cathodic pulse and an anodic pulse, with the interphase being between the cathodic pulse and the anodic pulse. The cathodic pulse may precede the anodic pulse. In another embodiment, the multiphasic waveform comprises a stimulation pulse and a recharge pulse, with the interphase being between the stimulation pulse and the recharge pulse. In still another embodiment, the multiphasic waveform comprises a stimulation pulse having a pulse width less than 100 μs, and the control circuitry is capable of varying the interphase of the multiphasic waveform in the range of 0 μs-100 μs.

In an optional embodiment, the control circuitry is capable of varying an amplitude of the multiphasic waveform. In this case, the control circuitry may be capable of discretely varying the amplitude of the multiphasic stimulation energy in a plurality of low-resolution steps, and may further be capable of varying the interphase of the multiphasic stimulation energy between the low-resolution steps; for example, by discretely varying the interphase in a plurality of high-resolution steps between each adjacent pair of low-resolution steps.

In another optional embodiment, the neurostimulation system further comprises memory capable of storing a set of stimulation parameters, in which case, the control circuitry may be capable of varying the interphase of the multiphasic waveform in accordance with the stimulation parameter set. The neurostimulation may further comprise telemetry circuitry capable of wirelessly receiving instructions from an external programmer to vary the interphase of the multiphasic waveform. The neurostimulation system may further comprise a case that contains the electrical contact(s), output stimulation circuitry, and control circuitry to form a neurostimulator that may be implantable.

In accordance with a third aspect of the present inventions, a programmer for a neurostimulator is provided. The programmer comprises a user interface capable of receiving an input from a user, and a processor capable of generating a plurality of stimulation parameter sets defining a multiphasic waveform in response to the user input, wherein at least some of the stimulation parameter sets define differing interphase values for the multiphasic waveform. The multiphasic waveform may have the same features described above. The programmer further comprises output circuitry capable of transmitting the plurality of stimulation parameter sets to a neurostimulator.

In an optional embodiment, at least some of the stimulation parameter sets define differing amplitude values for the multiphasic waveform. In this case, at least two of the stimulation parameter sets define different amplitude values, and a series of stimulation parameter sets between the at least two stimulation parameter sets define different interphase values. In another optional embodiment, the user interface comprises an actuator, in which case, the processor can be capable of generating the stimulation parameter sets in response to actuation of the actuator. For example, the processor may be capable of generating the stimulation sets in response to a single actuation of the actuator (e.g., by continuously pressing a button). In still another optional embodiment, the output circuitry may have telemetry circuitry capable of wirelessly transmitting the stimulation parameter sets to the neurostimulator.

In accordance with a fourth aspect of the present inventions, a computer readable medium for operating a tissue stimulation system is provided. The medium contains instructions, which when executed, comprise accessing look-up table(s) comprising a first series of states associated with a first amplitude value, the first series of states including a respective series of differing (e.g., gradually increasing) interphase values. The instructions, when executed, further comprise stepping through the first series of states, and generating a set of stimulation parameters defining a multiphasic wave for each state of the first series of states that has been stepped through. Each stimulation parameter set includes the first amplitude value and the interphase value included within the respective state. Each stimulation parameter set may further comprise a stimulation pulse width, a stimulation pulse rate, and a stimulation pulse width. The multiphasic wave can have the same features described above.

In one embodiment, the look-up table comprises a second series of states associated with a second amplitude value different from the first amplitude value, the second series of states including a respective series of gradually increasing interphase values for the multiphasic wave. In this case, the instructions, when executed, further comprise stepping through the second series of states, and generating a set of stimulation parameters for each state of the second series of states that has been stepped through, each stimulation parameter set comprising the second amplitude value and the interphase value included within the respective state.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 16 is one exemplary look-up table containing amplitude values and interphase values, which can be used by the HHP to generate stimulation parameters; and FIG. 17 is another exemplary look-up table containing amplitude values and interphase values, which can be used by the HHP to generate stimulation parameters.

DETAILED DESCRIPTION OF THE EMBODIMENTS

At the outset, it is noted that the present invention may be used with an implantable pulse generator (IPG), radio rate (RF) transmitter, or similar electrical stimulator, that may be used as a component of numerous different types of stimulation systems. The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
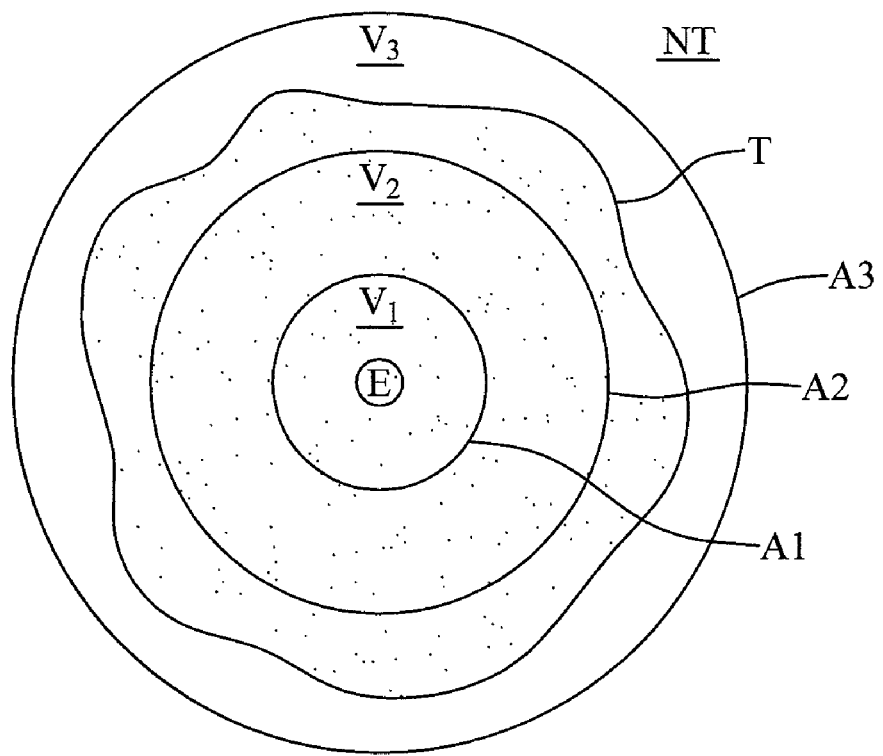
FIG. 1 is a diagram of varying volumes of activated tissue created by a prior art SCS system.
Figure 2:
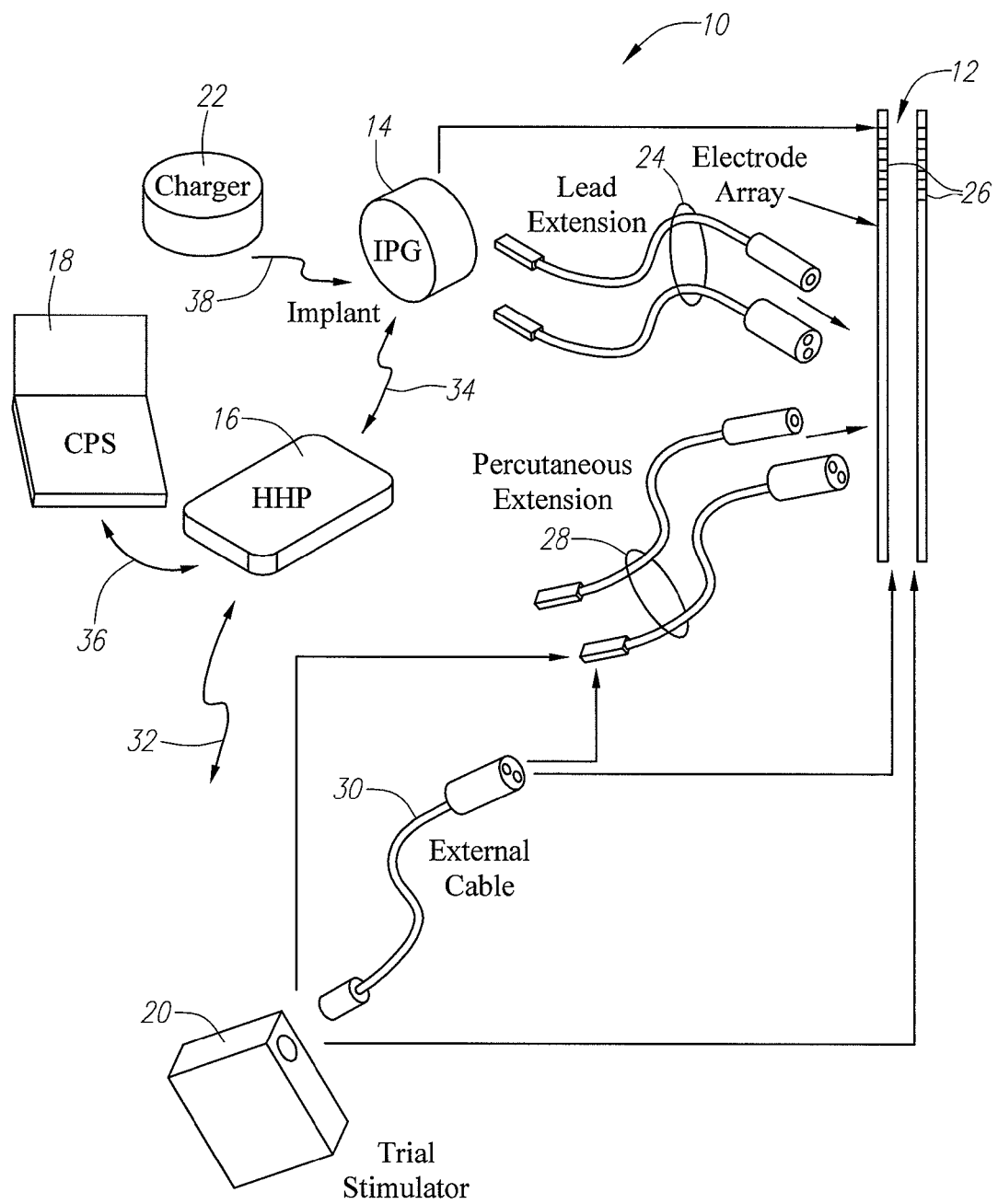
FIG. 2 is plan view of one embodiment of a spinal cord stimulation (SCS) system arranged in accordance with the present inventions.

Turning first to FIG. 2, an exemplary SCS system 10 generally includes one or more (in this case, two) implantable stimulation leads 12, an implantable pulse generator (IPG) 14 (or alternatively RF receiver-stimulator), an external hand-held programmer (HHP) 16, a Clinician's Programmer Station (CPS) 18, an External Trial Stimulator (ETS) 20, and an external charger 22.

Figure 3:
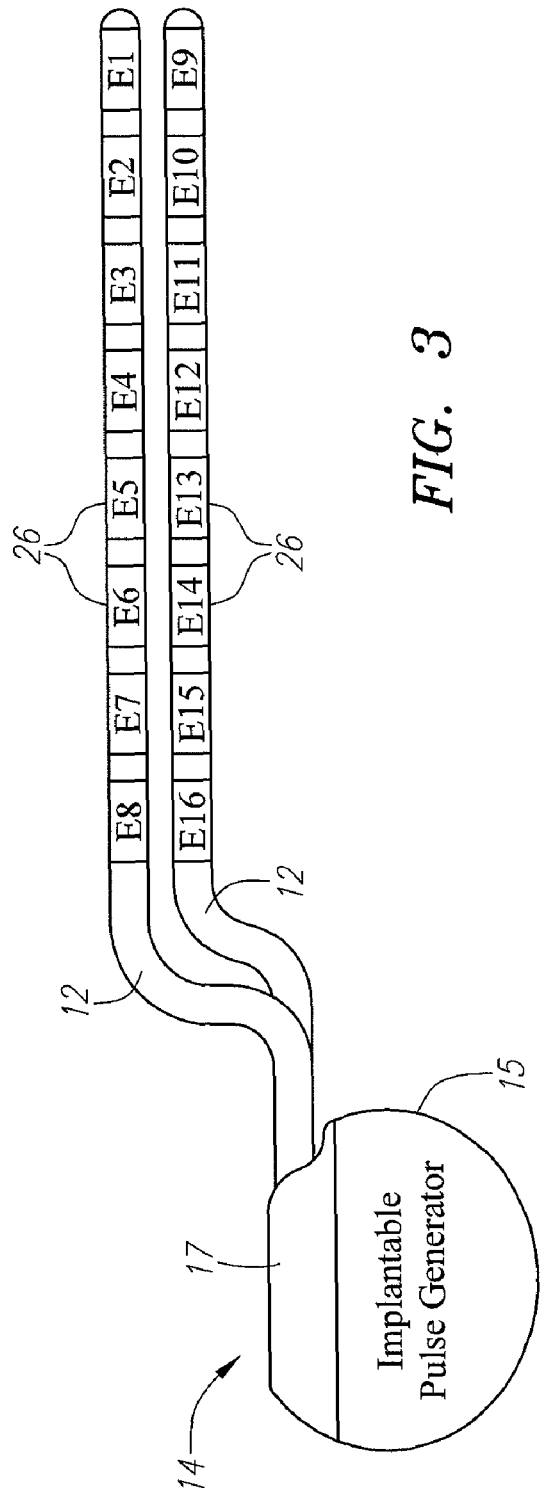
FIG. 3 is a profile view of an implantable pulse generator (IPG) used in the SCS system of FIG. 2.

The IPG 14 is physically connected via one or more percutaneous lead extensions 24 to the stimulation leads 12, which carry a plurality of electrodes 26 arranged in an array. In the illustrated embodiment, the stimulation leads 20 are percutaneous leads, and to this end, the electrodes 22 are arranged in-line along the stimulation leads 12. In the illustrated embodiment shown in FIG. 3, one stimulation lead 12 has eight electrodes 26 (labeled E1-E8), and the other stimulation lead 12 includes eight electrodes 26 (labeled E9-E16). The actual number and shape of leads and electrodes will, of course, vary according to the intended application. Alternatively, the stimulation leads 20 may be replaced with a single paddle stimulation lead. The IPG 14 comprises an outer case 15 for housing the electronic and other components (described in further detail below), and a connector 17 in which the proximal end of the stimulation lead 12 mates in a manner that electrically couples the electrodes 26 to the electronics within the outer case 15. The outer case 15 is composed of an electrically conductive, biocompatible material, such as titanium, and forms a hermetically sealed compartment wherein the internal electronics are protected from the body tissue and fluids. In some cases, the outer case 15 serves as an electrode, as will be described in further detail below.

As will be described in further detail below, the IPG 14 includes pulse generation circuitry that delivers the electrical stimulation energy to the electrode array 26 in accordance with a set of stimulation parameters. Such stimulation parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrode array 26), pulse duration (measured in microseconds), and pulse rate (measured in pulses per second). Significantly, as will be described in further detail below, the electrical stimulation energy provided by the IPG 14 is multiphasic stimulation energy, and in particular biphasic stimulation energy, that includes an adjustable interphase (i.e., time period between the pulses of the biphasic pulse). To this end, the stimulation pulse parameters also include an interphase value (measuring in microseconds).

With respect to the stimulus patterns provided during operation of the SCS system 10, electrodes that are selected to transmit or receive stimulation energy are referred to herein as "activated," while electrodes that are not selected to transmit or receive stimulation energy are referred to herein as "nonactivated" or "off." Electrical stimulation will occur between two (or more) activated electrodes, one of which may be the IPG case. Simulation energy may be transmitted to the tissue in a monopolar or multipolar (e.g., bipolar, tripolar, etc.) fashion.

Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

Figure 4:
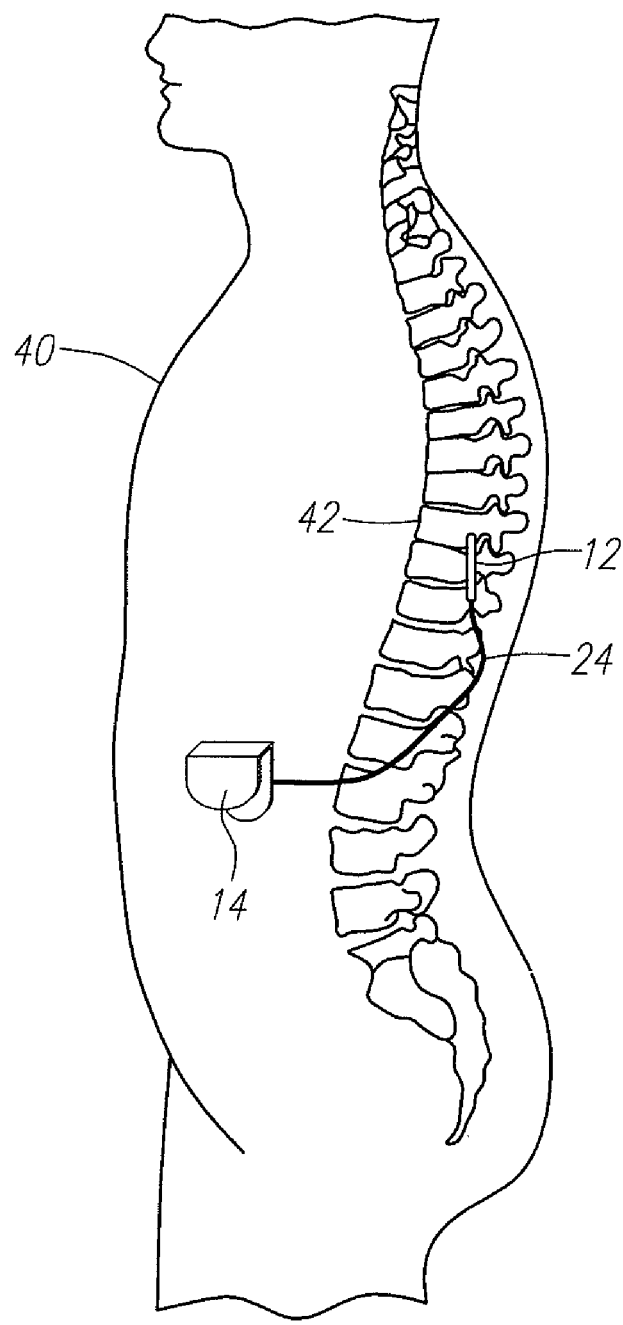
FIG. 4 is a plan view of the SCS system of FIG. 2 in use with a patient.

Referring to FIG. 4, the stimulation leads 12 are implanted within the spinal column 42 of a patient 40. The preferred placement of the stimulation leads 12 is adjacent, i.e., in the epidural space above the spinal cord area to be stimulated. Due to the lack of space near the location where the stimulation leads 12 exit the spinal column 40, the IPG 14 is generally implanted in a surgically-made pocket either in the abdomen or above the buttocks. The IPG 14 may, of course, also be implanted in other locations of the patient's body. The lead extension(s) 24 facilitate locating the IPG 14 away from the exit point of the stimulation leads 12. After implantation, the IPG 14 is used to provide the therapeutic stimulation under control of the patient.

Referring back to FIG. 2, the ETS 20 may also be physically connected via the percutaneous lead extensions 28 and external cable 30 to the stimulation leads 12. The ETS 20, which has similar pulse generation circuitry as the IPG 14, also delivers electrical multiphasic stimulation energy to the electrode array 26 in accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Further details of an exemplary ETS are described in U.S. Pat. No. 6,895,280, which is expressly incorporated herein by reference.

The HHP 16 may be used to telemetrically control the ETS 20 via a bi-directional RF communications link 32. Once the IPG 14 and stimulation leads 12 are implanted, the HHP 16 may be used to telemetrically control the IPG 14 via the RF communications link 30. Such control allows the IPG 14 to be turned on or off and to be programmed with different stimulation programs after implantation. Once the IPG 14 has been programmed, and its power source has been charged or otherwise replenished, the IPG 14 may function as programmed without the HHP 16 being present.

The CPS 18 provides clinician detailed stimulation parameters for programming the IPG 14 and ETS 20 in the operating room and in follow-up sessions. The CPS 18 may perform this function by indirectly communicating with the IPG 14 or ETS 20, through the HHP 16, via an IR communications link 36. Alternatively, the CPS 18 may directly communicate with the IPG 14 or ETS 20 via an RF communications link (not shown). The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference.

Figure 5:
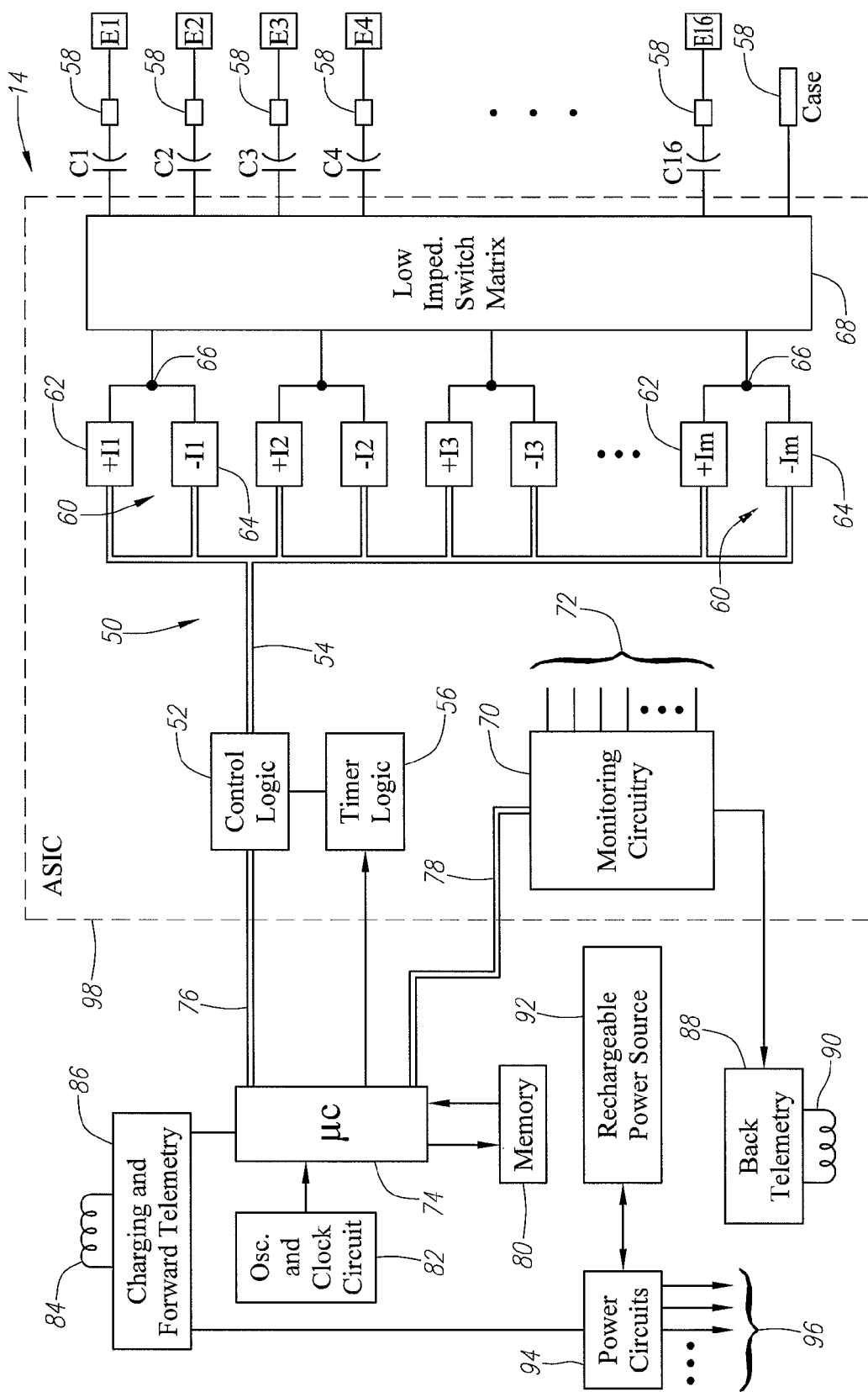
FIG. 5 is a block diagram of the internal components of the IPG of FIG. 3.

Turning next to FIG. 5, one exemplary embodiment of the IPG 14 will now be described. The IPG 14 includes stimulation output circuitry 50 capable of individually generating electrical stimulation pulses of a specified amplitude under control of control logic 52 over data bus 54. As will be described in further detail below, the stimulation output circuitry 50 is capable of outputting a multiphase waveform, and in particular, a biphasic waveform. The pulse rate, pulse width, and pulse interphase of the biphasic stimulation energy output by the IPG 14 is controlled using timer logic circuitry 56. The timer logic circuitry 56 may have a suitable resolution, e.g., 10 µs. The biphasic stimulation energy is supplied via capacitors C1-C16 to electrical contacts 58 corresponding to electrodes E1-E16 and the case electrode.

In the illustrated embodiment, the stimulation output circuitry 50 comprises a plurality m independent current source pairs 60 capable of supplying stimulation energy to the electrical contacts 58 at a specified and known amperage. One current source 62 of each pair 60 functions as a positive (+) or anodic current source, while the other current source 64 of each pair 60 functions as a negative (−) or cathodic current source. The outputs of the anodic current source 62 and the cathodic current source 64 of each pair 60 are connected to a common node 66. The stimulation output circuitry 50 further comprises a low impedance switching matrix 68 through which the common node 66 of each current source pair 60 is connected to any of the electrical contacts 58 via the capacitors C1-C16. Alternatively, the stimulation output circuitry 50 does not use a low impedance switching matrix 68, but rather uses a bi-directional current source for each of the electrical contacts 58.

Thus, for example, it is possible to program the first anodic current source 62 (+I1) to produce a pulse of +4 mA (at a specified rate and for a specified duration), and to synchronously program the second cathodic current source 64 (−I2) to similarly produce a pulse of −4 mA (at the same rate and pulse width), and then connect the node 86 of the anodic current source 62 (+I1) to the electrical contact 58 corresponding to electrode E3, and connect the node 66 of the cathodic current source 64 (−I2) to the electrical contact 58 corresponding to electrode E1.

Hence, it is seen that each of the programmable electrical contacts 58 can be programmed to have a positive (sourcing current), a negative (sinking current), or off (no current) polarity. Further, the amplitude of the current pulse being sourced or sunk from a given electrical contact 58 may be programmed to one of several discrete levels. In one embodiment, the current through each electrical contact 58 can be individually set from 0 to ±10 mA in steps of 100 µA, within the output voltage/current requirements of the IPG 14. Additionally, in one embodiment, the total current output by a group of electrical contacts 58 can be up to ±20 mA (distributed among the electrodes included in the group). Moreover, it is seen that each of the electrical contacts 58 can operate in a multipolar mode, e.g., where two or more electrical contacts are grouped to source/sink current at the same time. Alternatively, each of the electrical contacts 58 can operate in a monopolar mode where, e.g., the electrical contacts 58 are configured as cathodes (negative), and case of the IPG 14 is configured as an anode (positive).

It can be appreciated that an electrical contact 58 may be assigned an amplitude and included with any of up to k possible groups, where k is an integer corresponding to the number of channels, and in the preferred embodiment, is equal to 4, and with each channel k having a defined pulse width and pulse rate. Other channels may be realized in a similar manner. Thus, each channel identifies which electrical contacts 58 (and thus electrodes) are selected to synchronously source or sink current, the pulse amplitude at each of these electrical contacts, and the pulse width and pulse rate.

In an alternative embodiment, rather than using independent controlled current sources, independently controlled voltage sources for providing stimulation pulses of a specified and known voltage at the electrical contacts 58 can be provided. The operation of this output stimulation circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 further comprises monitoring circuitry 70 for monitoring the status of various nodes or other points 72 throughout the IPG 14, e.g., power supply voltages, temperature, battery voltage, and the like. The IPG 14 further comprises processing circuitry in the form of a microcontroller (μC) 74 that controls the control logic 52 over data bus 76, and obtains status data from the monitoring circuitry 70 via data bus 78. The IPG 14 additionally controls the timer logic 56. The IPG 14 further comprises memory 80 and oscillator and clock circuit 82 coupled to the microcontroller 74. The microcontroller 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the microcontroller 74 generates the necessary control and status signals, which allow the microcontroller 74 to control the operation of the IPG 14 in accordance with a selected operating program and stimulation parameters. In controlling the operation of the IPG 14, the microcontroller 74 is able to individually generate stimulus pulses at the electrodes 26 using the stimulation output circuitry 50, in combination with the control logic 52 and timer logic 56, thereby allowing each electrode 26 to be paired or grouped with other electrodes 26, including the monopolar case electrode, and to control the polarity, amplitude, rate, pulse width, interphase, and channel through which the current stimulus pulses are provided.

The IPG 14 further comprises an alternating current (AC) receiving coil 84 for receiving programming data (e.g., the operating program and/or stimulation parameters) from the HHP 16 in an appropriate modulated carrier signal, and charging and forward telemetry circuitry 86 for demodulating the carrier signal it receives through the AC receiving coil 84 to recover the programming data, which programming data is then stored within the memory 80, or within other memory elements (not shown) distributed throughout the IPG 14.

The IPG 14 further comprises back telemetry circuitry 88 and an alternating current (AC) transmission coil 90 for sending informational data sensed through the monitoring circuitry 70 to the HHP 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the HHP 16, all programmable settings stored within the IPG 14 may be uploaded to the HHP 16.

The IPG 14 further comprises a rechargeable power source 92 and power circuits 94 for providing the operating power to the IPG 14. The rechargeable power source 92 may, e.g., comprise a lithium-ion or lithium-ion polymer battery. The rechargeable battery 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits, also known as "inverter circuits") received by the AC receiving coil 84. To recharge the power source 92, an external charger (not shown), which generates the AC magnetic field, is placed against, or otherwise adjacent, to the patient's skin over the implanted IPG 14.

The AC magnetic field emitted by the external charger induces AC currents in the AC receiving coil 84. The charging and forward telemetry circuitry 86 rectifies the AC current to produce DC current, which is used to charge the power source 92. While the AC receiving coil 84 is described as being used for both wirelessly receiving communications (e.g., programming and control data) and charging energy from the external device, it should be appreciated that the AC receiving coil 84 can be arranged as a dedicated charging coil, while another coil, such as coil 90, can be used for bi-directional telemetry.

As shown in FIG. 5, much of the circuitry included within the IPG 14 may be realized on a single application specific integrated circuit (ASIC) 98. This allows the overall size of the IPG 14 to be quite small, and readily housed within a suitable hermetically-sealed case. Alternatively, most of the circuitry included within the IPG 14 may be located on multiple digital and analog dies, as described in U.S. patent application Ser. No. 11/177,503, filed Jul. 8, 2005, which is incorporated herein by reference in its entirety. For example, a processor chip, such as an application specific integrated circuit (ASIC), can be provided to perform the processing functions with on-board software. An analog IC (AIC) can be provided to perform several tasks necessary for the functionality of the IPG 14, including providing power regulation, stimulus output, impedance measurement and monitoring. A digital IC (DigIC) may be provided to function as the primary interface between the processor IC and analog IC by controlling and changing the stimulus levels and sequences of the current output by the stimulation circuitry in the analog IC when prompted by the processor IC.

It should be noted that the diagram of FIG. 5 is functional only, and is not intended to be limiting. Those of skill in the art, given the descriptions presented herein, should be able to readily fashion numerous types of IPG circuits, or equivalent circuits, that carry out the functions indicated and described. Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 6:
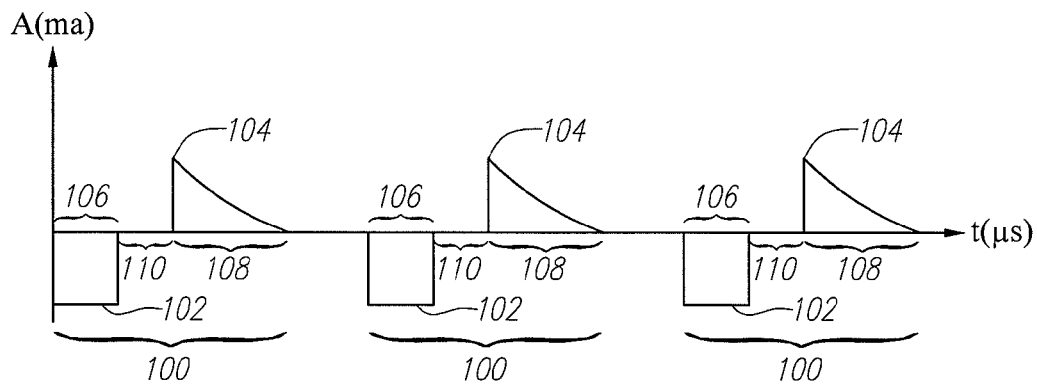
FIG. 6 is a timing diagram illustrating a series of biphasic pulses generated by the IPG of FIG. 5.

As briefly discussed above, the exemplary IPG 14 (or the ETS 20) generates a biphasic waveform, which, as illustrated in FIG. 6, includes a series of biphasic pulses 100, with each biphasic pulse 100 including a cathodic (negative) pulse 102 generated during a first phase period 106, and an anodic (positive) pulse 104 generated during a second phase period 108, with no pulse or portion thereof being generated during an interphase period 110 between the first and second phase periods 106, 108. As there shown, the cathodic pulse 102 is a square pulse, and the anodic pulse 104 is an exponentially decaying pulse.

In the illustrated embodiment, the first phase period 106 (pulse width of cathodic pulse 102) is programmable from 10 μs to 1000 μs in 10 μs steps. Preferably, the first phase period 106 is relatively short to maximize control over the tissue to be stimulated. For example, the first phase period 106 may be less than 200 μs, preferably less than 100 μs, and most preferably less than 50 μs. The second phase period 108 (pulse width of anodic pulse 104) is programmable from 10 μs to 6000 μs in 10 μs steps. Preferably, the second phase period 108 is relatively short on the same order as the first phase period 106. Notably, while the use of short pulse widths are useful for the SCS and other neurostimulation applications, the use of short pulse widths are particularly useful in DBS applications, as discussed in the background of the invention. Further details discussing DBS are discussed in U.S. Pat. No. 6,920,359, which is expressly incorporated herein by reference. As will be described in further detail below, the interphase period 110 is programmable from 0 μs to 100 μs in 10 μs steps. The pulse rate of the biphasic pulse 100 may be programmable in either a Normal Rate range, e.g., a range that covers 2 pps to 150 pps in 1 pps steps, or a High Rate range, e.g., a range that covers 150 pps to 350 pps in 10 pps steps, 400 pps to 500 pps in 50 pps steps, and 600 pps to 1200 pps in 100 pps steps.

In the illustrated embodiment, the cathodic pulse 102 serves as a depolarizing stimulation pulse (i.e., the pulse that evokes the action potential within the nerve tissue), and the anodic pulse 104 serves as a "recharge" pulse that prevents net DC charge transfer through the tissue. That is, charge is delivered through the electrode-tissue interface via the cathodic current during the first phase period 106, and then pulled back off the electrode-tissue interface via the oppositely polarized anodic current during the second phase period 108.

In the embodiment illustrated in FIG. 6, the first phase period 106 during which the cathodic pulse 102 is generated is an "active" phase period (i.e., a phase period during which electrical energy is provided to the electrodes by one or more current sources 60 (or alternatively, voltage sources) of the output circuitry 50 (shown in FIG. 5) that are turned on), and the second phase period 108 during which the anodic pulse 104 is generated is a "passive" phase period (i.e., a phase period during which electrical energy is provided to the electrodes via a recharge or redistribution of the charge flowing from any one or more of the coupling capacitors C1-C16, while the current sources or voltage sources of the output circuitry 50 are turned off).

Figure 7:
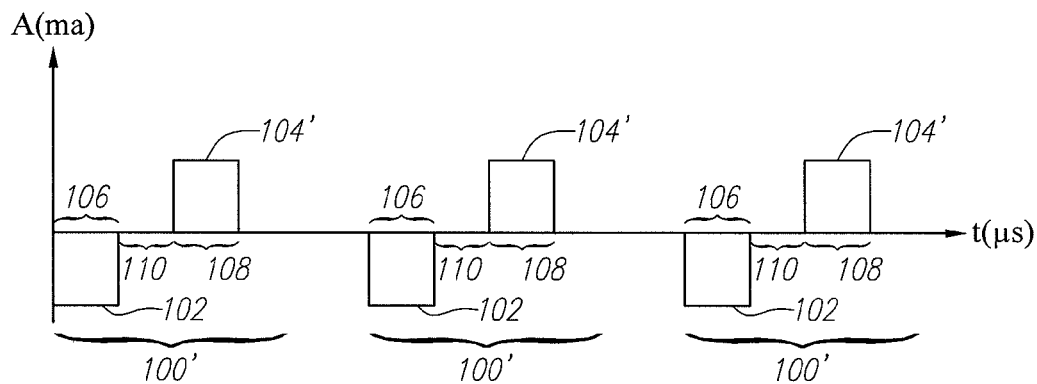
FIG. 7 is a timing diagram illustrating another series of biphasic pulses generated by the IPG of FIG. 5.

It should be noted that the anodic pulse 104 need not be generated during a passive phase period. Rather, as illustrated in FIG. 7, an exemplary biphasic pulse 100' has a second active phase period 108 during which an anodic pulse 104' is generated by turning on one or more of the current sources or voltage sources of the output circuitry 50. In the illustrated embodiment, the anodic pulse 104 is a square pulse having an amplitude such that a symmetrical biphasic waveform is created. Using this active recharge in this manner allows faster recharge while avoiding the charge imbalance that could otherwise occur. It should also be noted that a balanced charge condition could also be obtained without having a symmetrical biphasic pulse, if desired, by simply assuring that the total charge of the cathodic pulse of the biphasic pulse is equal to the total charge of the anodic pulse of the biphasic pulse.

Figure 8:
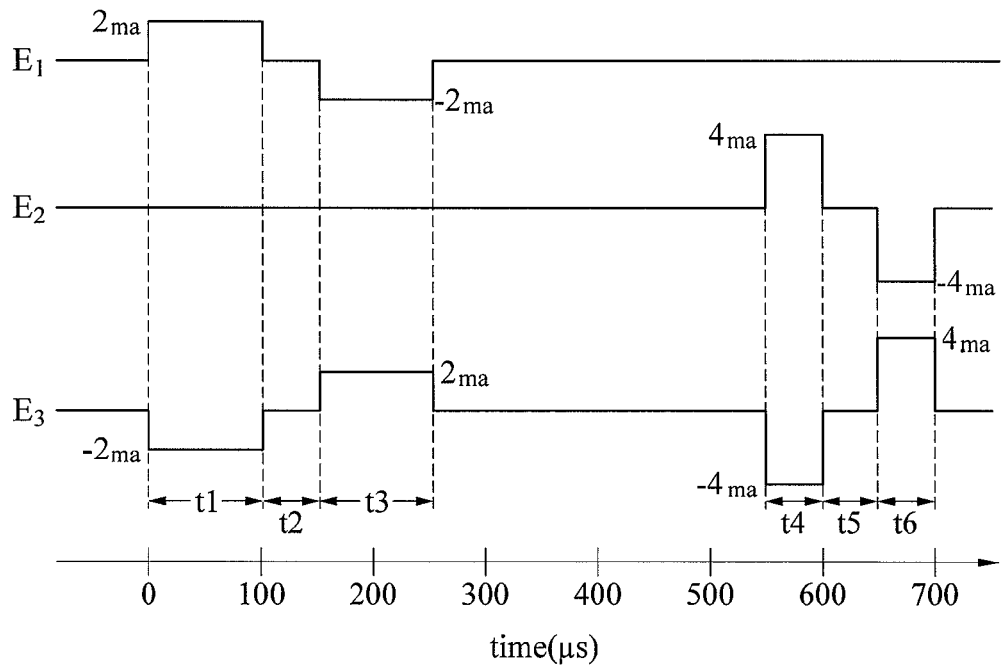
FIG. 8 is a timing diagram illustrating a series of biphasic pulses generated over multiple channels in a bipolar manner by the IPG of FIG. 5.

Referring to FIG. 8, an exemplary protocol for applying symmetrical biphasic pulses to the electrodes in a bipolar mode over multiple channels will be described. Beginning at 0 μs, electrode $E_1$ is programmed to produce a first phase current of +2 mA (anode) at the same time that electrode $E_3$ is programmed to produce first phase current of −2 mA (cathode) during a first phase period (pulse width) $t_1$. At the conclusion of the first phase period $t_1$, an interphase period $t_2$ is programmed after which the electrode $E_1$ is programmed to produce a second phase current of −2 mA (cathode) at the same time that electrode $E_3$ is programmed to produce a second phase current of +2 mA (anode) during a second phase period (pulsewidth) $t_3$. Each of the first phase period $t_1$ and the second phase period $t_3$ is programmed to last about 100 μs, thereby creating a symmetrical biphasic current pulse and a balanced charge condition, and the interphase period $t_2$ is programmed to last about 50 μs.

Beginning at 550 μs, electrode $E_2$ is programmed to produce a first phase current of +4 mA (anode) at the same time that electrode $E_3$ is programmed to produce first phase current of −4 mA (cathode) during a first phase period $t_4$. At the conclusion of the first phase period (pulsewidth) $t_4$, an interphase period $t_5$ is programmed after which the electrode $E_2$ is programmed to produce a second phase current of −4 mA (cathode) at the same time that electrode $E_3$ is programmed to produce a second phase current of +4 mA (anode) during a second phase period (pulsewidth) $t_6$. Each of the first phase period $t_4$ and the second phase period $t_6$ is programmed to last about 50 μs, thereby creating a symmetrical biphasic current pulse and a balanced charge condition. The interphase period $t_5$ is programmed to last about 50 μs.

Figure 9:
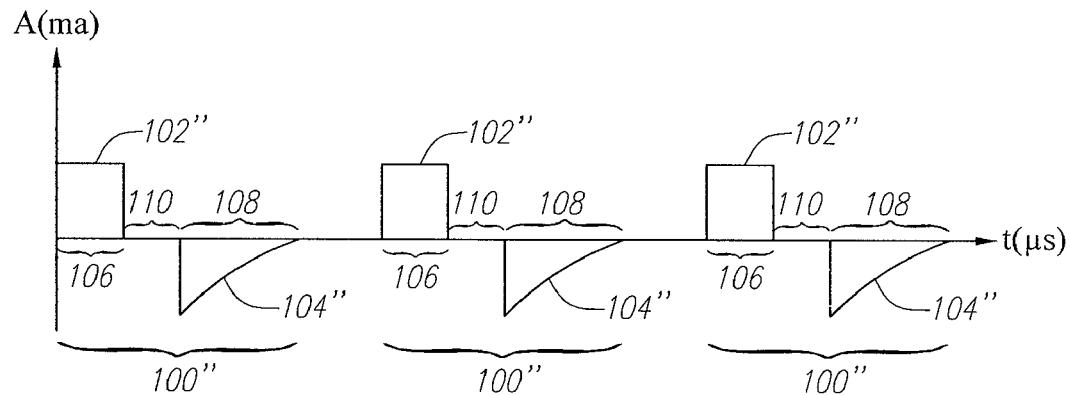
FIG. 9 is a timing diagram illustrating still another series of biphasic pulses generated by the IPG of FIG. 5.
Figure 10:
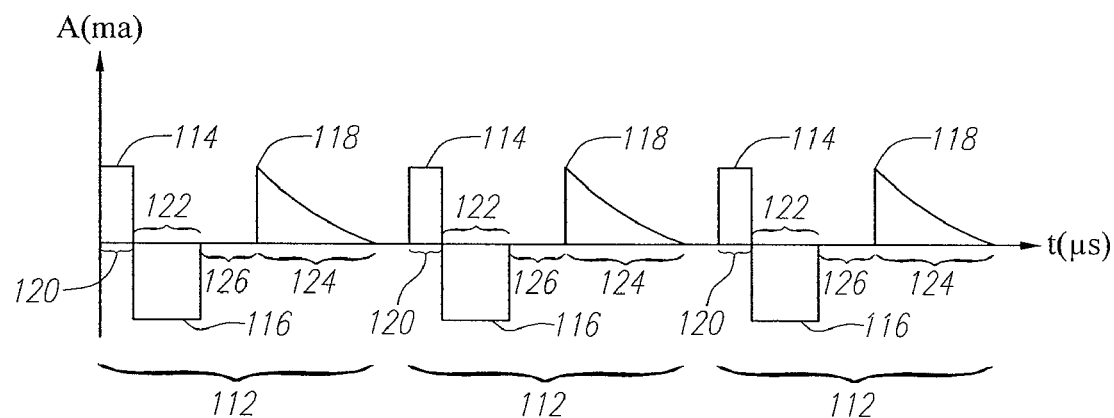
FIG. 10 is a timing diagram illustrating a series of triphasic pulses generated by the IPG of FIG. 5.

While the foregoing embodiments have been described as generating biphasic pulses having a cathodic pulse generated during a first phase period and an anodic pulse generated during a second phase period, alternative embodiments may generate biphasic pulses 100" having an anodic pulse 102" generated during the first phase period 106 and a cathodic pulse 104" generated during the second phase period 108 after the interphase period 110, with the anodic pulse being the stimulation pulse, and the cathodic pulse being the conditioning and/or recharge pulse, as illustrated in FIG. 9. The specific arrangement of the biphasic pulses may ultimately depend on the orientation of the nerve tissue relative to the electrodes. In other alternative embodiments, triphasic pulses may be generated. For example, as illustrated in FIG. 10, triphasic pulses 112 having a conditioning hyperpolarizing anodic pulse 114 generated during a first phase period 120, a depolarizing cathodic stimulation pulse 116 generated during a second phase period 122, and after an interphase period 126, a conditioning and/or recharge anodic pulse 118 generated during a third phase period 124.

Figure 11:
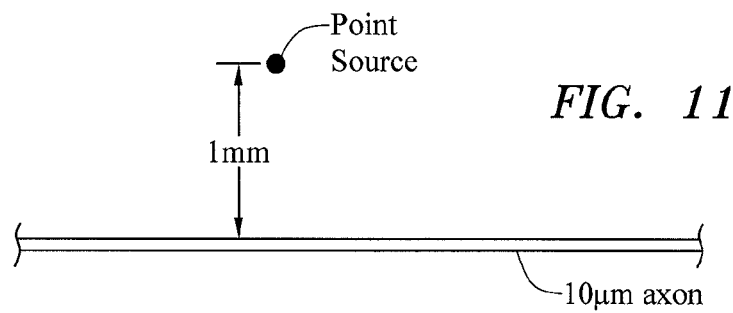
FIG. 11 is a plan view of an electrode point source adjacent a nerve axon that can be modeled to determine the action potential effect of electrical energy delivered from the point source to the nerve axon.
Figure 12:
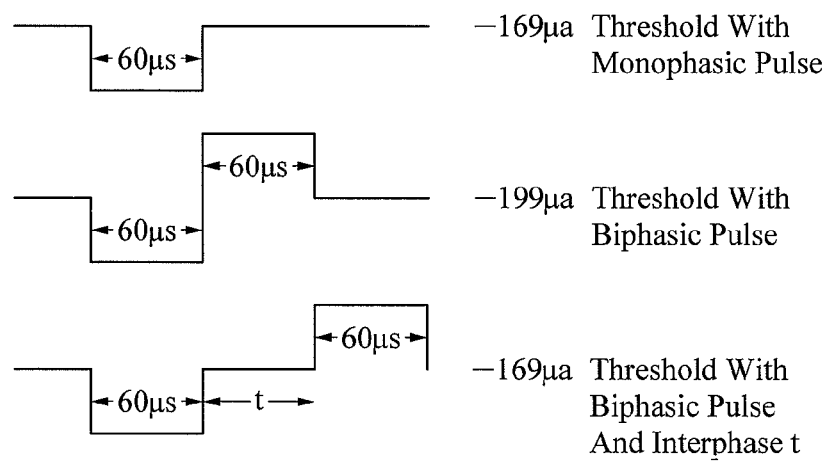
FIG. 12 are diagrams of a monophasic pulse, a biphasic pulse with no interphase, and a biphasic pulse with interphase that have been modeled using the point source and nerve axon illustrated in FIG. 11.

Significantly, the interphase of a biphasic (or multiphasic) pulse can be adjusted to alter the threshold at which a nerve is activated. For example, based on a non-linear computational model of a 10 μm diameter axon located 1 mm from a monopolar point source electrode (shown in FIG. 11), and assuming an isotropic and infinite electrical medium, it has been shown that the threshold at which an anodic monophasic pulse having a stimulation pulse width of 60 μs activates (evokes an action potential in) the axon is −169 μA, and the threshold at which a symmetrical biphasic pulse having anodic and cathodic pulse widths each of 60 μs and an interphase of 0 μs activates the axon is −199 μA. Thus, the interphase can be varied from 0 μs to a particular value where the cathodic pulse does not condition the axon (effectively providing an anodic monophasic pulse), thereby allowing the threshold of the axon to be varied in the range of −169 μA and −199 μA without varying the amplitude of the biphasic pulse, as shown in FIG. 12.

Based on this, the volume of activated tissue can be modified by modifying the interphase of the biphasic pulse between incremental adjustments in pulse amplitude, thereby effectively increasing the resolution of the stimulation energy that would not otherwise be afforded by only adjusting the pulse amplitude. In particular, the pulse amplitude can be graduated to modify the volume of activated tissue in relatively low resolution steps, and the interphase can be graduated to modify the volume of activated tissue in relatively high resolution steps between the low resolution steps associated with the pulse amplitude graduation.

Figure 13:
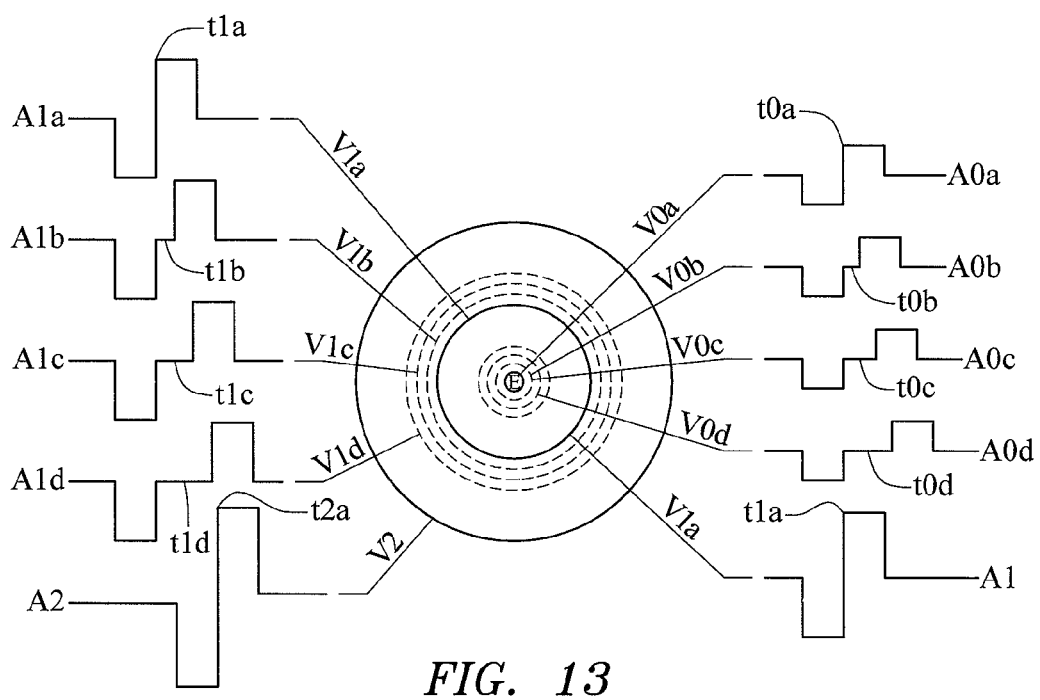
FIG. 13 is a diagram of varying volumes of tissue that can be activated by varying the interphase and amplitude of a biphasic pulse generated by the IPG of FIG. 3.

For example, referring to FIG. 13, an electrode E is shown applying biphasic pulses of differing interphases and amplitudes to create differing volumes of activated tissue (solid lines representing volumes of activated tissue at the resolution of the amplitude (in this case, when the interphase value equals 0), and dashed lines represent volumes of activated tissue between the resolution of the amplitude). At a pulse amplitude of $A0_a$ and an interphase $t0_a$ of 0 μs, a volume of activated tissue $V0_a$ is created. As the interphase is discretely increased ($t0_b$, $t0_c$, $t0_d$, and so on), discretely increasing volumes of activated tissue $V0_b$, $V0_c$, $V0_d$, and so on, are created. At an increased pulse amplitude of A1 and an interphase $t1_a$ of 0 μs, an increased volume of activated tissue $V1_a$ is created. As the interphase is again discretely increased ($t1_D$, $t1_c$, $t1_d$, and so on), discretely increasing volumes of activated tissue $V1_b$, $V1_c$, $V1_d$, and so on, are created. At an increased pulse amplitude of A2 and an interphase $t2_a$ of 0 μs, an increased volume of activated tissue $V2_a$ is created. This process can be repeated to create larger volumes of activated tissue. Of course, the pulse amplitude and/or interphase of the biphasic pulses can be discretely decreased to discretely create smaller volumes of activated tissue.

In the illustrated embodiment, the pulse amplitude is graduated in uniform steps, such that A1=A0+δ1, A2=A1+δ1, and so on, where δ1 is a step size equal to a fixed value, and preferably the smallest step size of the stimulation output circuitry, e.g., 100 μa. Likewise, the interphase is graduated in uniform steps, such that $t0_b$=$t0_a$+δ2, $t0_c$=$t0_b$+δ2, $t0_d$=$t0_c$+δ2, $t1_b$=$t1_a$+δ2, $t1_c$=$t1_b$+δ2, $t1_d$=$t1_c$+δ2, and so on, where δ2 is a step size equal to a fixed value, and preferably the smallest step size of the timing circuitry, e.g., 10 μs. It should be noted, however, that although the use of uniform step sizes for the pulse amplitude and pulse interphase graduations is preferable, the steps sizes can conceivably be non-uniform.

Notably, the increase in resolution of the stimulation energy provided by adjusting the interphase (i.e., the number of interphase graduations between changes in pulse amplitude) will vary depending on the interphase step size, and ultimately, the time resolution of the hardware in the IPG 14. However, it is contemplated that, given a time resolution of 10 μs and a pulse amplitude resolution of 100 μA, adjustment of the interphase increases the resolution of the stimulation energy in the range of 5-10 times (i.e., 5-10 graduations of interphase between changes in pulse amplitude) greater than that when only the pulse amplitude is adjusted.

It should be noted that the number of interphase graduations between the changes in pulse amplitude may not be uniform if the interphase is reset to 0 each time the pulse amplitude is changed. That is, only the number of interphase graduations required to increase the volume of activated tissue associated with one pulse amplitude to the volume of activated tissue associated with the next pulse amplitude is needed, which number of interphase graduations may vary depending which adjacent pair of pulse amplitudes the interphase graduations are between. Alternatively, the number of interphase graduations between the pulse amplitude graduations is uniform, in which case, the interphase may not be 0 at each pulse amplitude graduation. It should also be noted that although the IPG 14 has been described as generating the multiphasic energy, the ETS 34 may also generate the multiphasic energy in the same manner described herein.

As briefly discussed above, the interphase, along with the other stimulation parameters, stored in the IPG 14 can be modified by the HHP 16 and/or CPS 18, thereby modifying the characteristics of the stimulation energy generated and output by the IPG 14 to the electrode. In the illustrated embodiment, this is accomplished by telemetrically transmitting instructions containing the stimulation parameters from the IPG 14 and/or CPS 18 to the IPG 14. Alternatively, instructions without the stimulation parameters can be transmitted from the HHP 16 and/or CPS 18 to the IPG 14 to otherwise change the stimulation parameters stored in the IPG 14.

Figure 14:
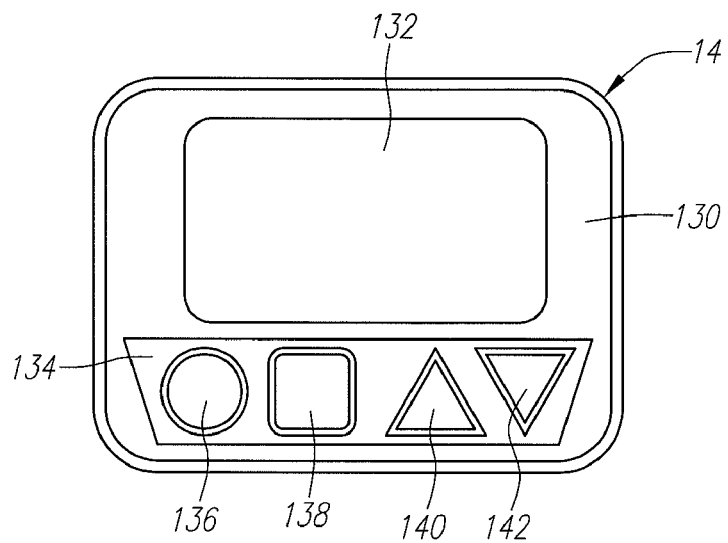
FIG. 14 is a plan view of a hand-held patient programmer (HHP) that can be used in the neurostimulation system of FIG. 2.

Referring now to FIG. 14, one exemplary embodiment of an HHP 16 will now be described. As previously discussed, the HHP 16 is capable of communicating with the IPG 14, ETS 20, or CPS 18. The HHP 16 comprises a casing 130, which houses internal componentry (including a printed circuit board (PCB)), and a lighted display screen 132 and a button pad 134 carried by the exterior of the casing 130. In the illustrated embodiment, the display screen 132 is a lighted flat panel display screen, and the button pad 134 comprises a membrane switch with metal domes positioned over a flex circuit, and a keypad connector connected directly to a PCB. The button pad 134 includes a series of buttons 136, 138, 140, and 142, which allow the IPG 14 to be turned ON and OFF, provide for the adjustment or setting of stimulation parameters within the IPG 14, and provide for selection between screens.

In the illustrated embodiment, the button 136 serves as an ON/OFF button that can be actuated to turn the IPG 14 ON and OFF. The button 138 serves as a select button that allows the HHP 16 to switch between screen displays and/or parameters. The buttons 140 and 142 serve as up/down buttons that can actuated to increment or decrement any of stimulation parameters of the biphasic pulse generated by the IPG 14 (or ETS 20), including amplitude, pulse width, and pulse rate. For example, the selection button 138 can be actuated to place the HHP 16 in an "Amplitude Adjustment Mode," during which the biphasic pulse amplitude can be adjusted via the up/down buttons 140, 142, a "Pulse Width Adjustment Mode," during which the biphasic pulse width can be adjusted via the up/down buttons 140, 142, and a "Pulse Rate Adjustment Mode," during which the biphasic pulse rate can be adjusted via the up/down buttons 140, 142. Alternatively, dedicated up/down buttons can be provided for each stimulation parameter. As will be described in further detail below, actuation of the up/down buttons 140, 142 during the "Pulse Amplitude Adjustment Mode" will also increment or decrement the interphase of the biphasic pulses. Duration actuation of the up/down buttons 140, 142, the present values of the amplitude/interphase, pulse width and pulse rate may be displayed on the display screen 132 during the respective adjustment modes. Alternatively, rather than using up/down buttons, any other type of actuator, such as a dial, slider bar, or keypad, can be used to increment or decrement the interphase of the biphasic pulses.

Figure 15:
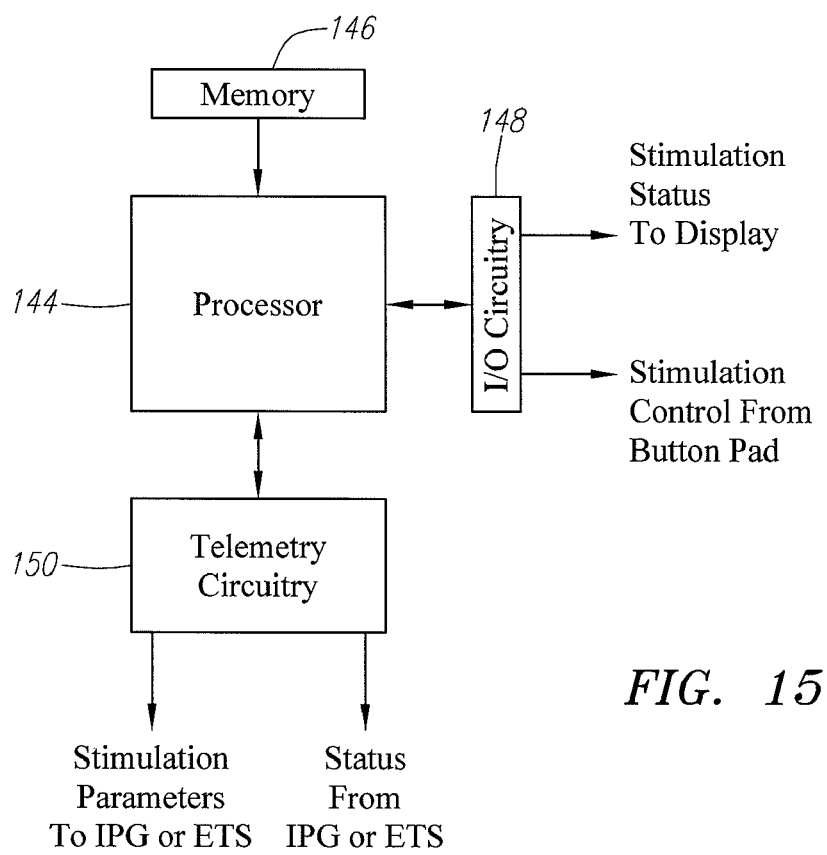
FIG. 15 is a block diagram of the internal components of the HHP of FIG. 14.

Referring to FIG. 15, the internal components of an exemplary HHP 16 will now be described. The HHP 16 generally includes a processor 144 (e.g., a microcontroller), memory 146 that stores an operating program for execution by the processor 144, as well as stimulation parameter sets in a look-up table (described below), input/output circuitry, and in particular, telemetry circuitry 148 for outputting stimulation parameters to the IPG 14 and receiving status information from the IPG 14, and input/output circuitry 150 for receiving stimulation control signals from the button pad 134 and transmitting status information to the display screen 132 (shown in FIG. 14). As well as controlling other functions of the HHP 16, which will not be described herein for purposes of brevity, the processor 144 generates new stimulation parameter sets in response to the user operation of the button pad 134. These new stimulation parameter sets would then be transmitted to the IPG 14 (or EPS 20) via the telemetry circuitry 148. Further details of the functionality and internal componentry of the HHP 16 are disclosed in U.S. Pat. No. 6,895,280, which has previously been incorporated herein by reference.

With respect to any modification to the pulse width and pulse rate, the processor 144 simply increments or decrements these parameters accordingly as the up/down buttons 140, 142 are actuated. With respect to the pulse amplitude and pulse interphase, the processor 144 accesses a look-up table 152 before generating the stimulation parameter sets. That is, in contrast to the conventional technique of merely incrementing/decrementing the pulse amplitude in response to actuation of the up/down buttons 140, 142, the processor 144 increases the resolution of the stimulation energy by adjusting the pulse interphase between adjustments in the pulse amplitude much like in the manner shown in FIG. 13.

To this end, an exemplary look-up table 152 illustrated in FIG. 16 includes a multitude of states each having a pulse amplitude value and a interphase value. As there shown, the states can be grouped into several series, with each series including a single amplitude value and a respective series of gradually increasing interphase values. That is, the states are grouped into several series at the resolution of the pulse amplitude. The amplitude values associated with the respective series of states gradually increases from one series to the next. For example, series 1 (states 1-5) is associated with an amplitude value of 100 µA and respectively includes interphase values of 0 µs, 10 µs, 20 µs, 30 µs, and 40 µs. Series 2 (states 6-12) is associated with an amplitude value of 200 µA and respectively includes interphase values of 0 µs, 10 µs, 20 µs, 30 µs, 40 µs, 50 µs, 60 µs, and 70 µs. Series 3 (states 13-16) is associated with an amplitude value of 300 µA and respectively includes interphase values of 0 µs, 10 µs, 20 µs, and 30 µs.

Although the first state of each series of states (i.e., at the amplitude resolution) has an interphase value of 0, these initial interphase values can be a value other than 0, depending on the manner in which the look-up table is generated (described in further detail below). For example, FIG. 17 illustrates another exemplary look-up table 154 that is similar to the previous look-up table 152, with the exception that some of the interphase values at the beginning of each series of states are non-zero. For example, series 1 (states 1-6) is associated with an amplitude value of 100 µA and respectively includes interphase values of 0 µs, 10 µs, 20 µs, 30 µs, 40 µs, and 50 µs. Series 2 (states 7-10) is associated with an amplitude value of 200 µA and respectively includes interphase values of 30 µs, 40 µs, 50 µs, and 60 µs. Series 3 (states 11-16) is associated with an amplitude value of 300 µA and respectively includes interphase values of 10 µs, 20 µs, 30 µs, 40 µs, 50 µs, and 60 µs.

In each of the look-up tables 152, 154, the amplitude values are incremented (going down the look-up tables) in uniform steps equal to the maximum current resolution (e.g., smallest step is 100 µA) of the hardware, and the interphase values are incremented (going down the look-up tables) in uniform steps equal to the maximum time resolution (e.g., smallest step of 10 µs) of the hardware. However, in alternative embodiments, the amplitude value and interphase value step sizes need not be uniform. For example, an interphase value may jump from 10 µs to 30 µs within the same series of states. Or an amplitude value may jump from 100 µA to 300 µA if the graduation of interphase values can span the entire first and second series of states. Notably, at least with respect to look-up table 152, the number of states in each series differs, because the action potential evoking effect of the stimulation energy is not uniform over changes in pulse amplitude/interphase. With respect to the look-up table 154, the number of states in each series may differ also because the interphase value is not reset to 0 at the beginning of each series of states.

Generation of the look-up tables can be accomplished by modeling a nerve fiber in relation to a point electrode source (shown in FIG. 11) with a biphasic waveform and uniformly varying the distance between the nerve fiber and point source to determine the pulse amplitude and interphase of the biphasic waveform at which an action potential is evoked within the nerve fiber for the different distances. Of course, other more sophisticated models that include, for instance, more orientations of nerve fibers, inhomogenous media and finite sized electrodes can be used.

For example, to generate the first state in the look-up table 152, while the amplitude value is set to the minimum value (100 µA) and the interphase value is set to 0, the maximum distance between the point source and nerve fiber that an action potential will be evoked in the nerve fiber ("maximum action potential distance") is determined. Next, while the interphase value is set to 0, the amplitude value is incremented to the next higher value (200 µA), and the maximum action potential distance is again determined. The amplitude value is then reset back to the previous value (100 µA), while the interphase is repeatedly incremented (by 10 µs) to determine the interphase value at which the maximum action potential distance is greater than the maximum action potential distance corresponding to the next highest value amplitude value (200 µA) is greater. Based on this knowledge, the number of interphase adjustments necessary to extend from the first state to the incremented amplitude state is determined, and states comprising different interphase values are then created between the states with the different amplitude (0 interphase states).

Another method of generating a look-up table may involve repeatedly incrementing the interphase value at a specific amplitude pulse value while determining the maximum action potential distance (by moving the point source) for each interphase increment until there is no effect on the biphasic stimulation (i.e., the biphasic pulse effectively turns into a monophasic pulse). Next, the distance of the point source is incremented (about the distance associated with a single interphase graduation), the amplitude pulse value is then incremented, and the lowest interphase required to evoke in action potential at the new distance is determined. The interphase value is then repeatedly incremented again for the new amplitude value. This process may result in a look-up table that looks similar to the look-up table 154 illustrated in FIG. 17.

Thus, it can be appreciated from the foregoing, that the processor 144 in the HHP 16 can gradually increase the volume of activated tissue by stepping down through the states of the look-up table 152 (or look-up table 154) in response to actuation of the up button 140, and can gradually decrease the volume of activated tissue by stepping up through the states of the look-up table 152 (or look-up table 154) in response to actuation of the down button 142. For each state that is stepped through, the processor generates a set of stimulation parameters (which defines a biphasic wave) comprises the corresponding amplitude value and phase value for that state, as well as another parameters (e.g., pulse width and pulse rate), and wirelessly transmits the stimulation parameter set to the IPG 14 (or ETS 20), which in turn, modifies the stimulation energy output by the IPG 14 (or ETS 20) in accordance with the new stimulation parameters.

Notably, although the look-up tables 152, 154 are generally programmed into the HHP 16 during its manufacture, the look-up tables 152, 154 may alternatively be manually programmed into the HHP 16 via a suitable user interface. Also, while look-up tables 152, 154 have been described as being accessed to sequentially change the amplitude values and interphase values as the up/down buttons 140, 142 are actuated, an analytical formula may alternatively be used to sequentially change the amplitude values and interphase values.

As briefly discussed above, modifying the stimulation parameters in the programmable memory of the IPG 14 after implantation can also be performed by a physician or clinician using the CPS 18, which can directly communicate with the IPG 14 or indirectly communicate with the IPG 14 via the HHP 16. As shown in FIG. 2, the overall appearance of the CPS 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CPS 18. Alternatively, such programming methodologies can be performed using firmware or hardware. In any event, the CPS 18 may actively control the characteristics of the electrical stimulation generated by the IPG 14 (or ETS 20) to allow the optimum stimulation parameters to be determined based on patient feedback and for subsequently programming the IPG 14 (or ETS 20) with the optimum stimulation parameters. The same types of look-up tables 152, 154 illustrated in FIGS. 16 and 17, can be stored and used by the CPS 18 to gradually increase or decrease the volume of activated tissue by the IPG 14 (or ETS 20). Further details discussing CPSs are disclosed in U.S. Pat. No. 6,909,917, which is expressly incorporated herein by reference.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation system, comprising:
   one or more electrical contacts;
   output stimulation circuitry capable of outputting a multiphasic waveform to the one or more electrical contacts; and
   control circuitry capable of varying an interphase and an amplitude of the multiphasic stimulation waveform in response to a single actuation of an actuator, wherein the amplitude of the multiphasic waveform is varied from a first non-zero value to a second different non-zero value.

2. A method of providing therapy to a patient using the neurostimulation system of claim 1, comprising:
   placing one or more electrodes in contact with tissue of a patient;
   delivering multiphasic stimulation energy from the neurostimulation system to the one or more electrodes, thereby activating a volume of the tissue; and
   modifying the volume of activated tissue by varying the interphase and the amplitude of the multiphasic stimulation energy being delivered to the one or more electrodes in response to the single actuation of the actuator.

3. The method of claim 2, wherein the multiphasic stimulation energy is biphasic stimulation energy.

4. The method of claim 2, wherein the multiphasic stimulation energy comprises a cathodic pulse and an anodic pulse, and wherein the interphase is between the cathodic pulse and the anodic pulse.

5. The method of claim 4, wherein the cathodic pulse precedes the anodic pulse.

6. The method of claim 2, wherein the multiphasic stimulation energy comprises a stimulation pulse and a recharge pulse, and wherein the interphase is between the stimulation pulse and the recharge pulse.

7. The method of claim 2, wherein the multiphasic stimulation energy comprises a stimulation pulse having a pulse width less than 100 µs.

8. The method of claim 2, wherein the interphase of the multiphasic energy is varied in the range of 0 µs-100 µs.

9. The method of claim 2, wherein the amplitude of the multiphasic stimulation energy is discretely varied in a plurality of steps, and the interphase of the multiphasic stimulation energy is varied between the plurality of steps.

10. The method of claim 9, wherein the amplitude variation modifies the volume of activated tissue in low resolution steps, and wherein the interphase variation modifies the volume of activated tissue in high resolution steps between the low resolution steps.

11. The neurostimulation system of claim 1, further comprising a stimulation lead carrying at least one electrode electrically coupled to the one or more electrical contacts.

12. The neurostimulation system of claim 1, wherein the multiphasic waveform is a biphasic waveform.

13. The neurostimulation system of claim 1, wherein the multiphasic waveform comprises a cathodic pulse and an anodic pulse, and wherein the interphase is between the cathodic pulse and the anodic pulse.

14. The neurostimulation system of claim 13, wherein the cathodic pulse precedes the anodic pulse.

15. The neurostimulation system of claim 1, wherein the multiphasic waveform comprises a stimulation pulse and a recharge pulse, and wherein the interphase is between the stimulation pulse and the recharge pulse.

16. The neurostimulation system of claim 1, wherein the multiphasic waveform comprises a stimulation pulse having a pulse width less than 100 µs.

17. The neurostimulation system of claim 1, wherein the control circuitry is capable of varying the interphase of the multiphasic waveform in the range of 0 µs-100 µs.

18. The neurostimulation system of claim 1, wherein the control circuitry is capable of discretely varying the amplitude of the multiphasic stimulation energy in a plurality of low-resolution steps, and is capable of varying the interphase of the multiphasic stimulation energy between the low-resolution steps in response to the single actuation of the actuator.

19. The neurostimulation system of claim 18, wherein the control circuitry is capable of discretely varying the interphase in a plurality of high-resolution steps between each adjacent pair of low-resolution steps in response to the single actuation of the actuator.

20. The neurostimulation system of claim 1, further comprising memory capable of storing a set of stimulation parameters, wherein the control circuitry is capable of varying the interphase and the amplitude of the multiphasic waveform in accordance with the stimulation parameter set.

21. The neurostimulation system of claim 1, further comprising telemetry circuitry capable of wirelessly receiving instructions from an external programmer to vary the interphase and the amplitude of the multiphasic waveform.

22. The neurostimulation system of claim 1, further comprising a case, wherein the one or more electrical contacts, output stimulation circuitry, and control circuitry are contained in the case to form a neurostimulator.

23. The neurostimulation system of claim 22, wherein the neurostimulator is implantable.

24. The neurostimulation system of claim 1, wherein the control circuitry is capable of separately varying the interphase and the amplitude of the multiphasic stimulation energy in response to the single actuation of the actuator.

25. The neurostimulation system of claim 1, wherein the control circuitry is capable of varying the interphase of the multiphasic stimulation energy at different amplitudes of the multiphasic stimulation energy in response to the single actuation of the actuator.

\* \* \* \* \*